Figure 1:
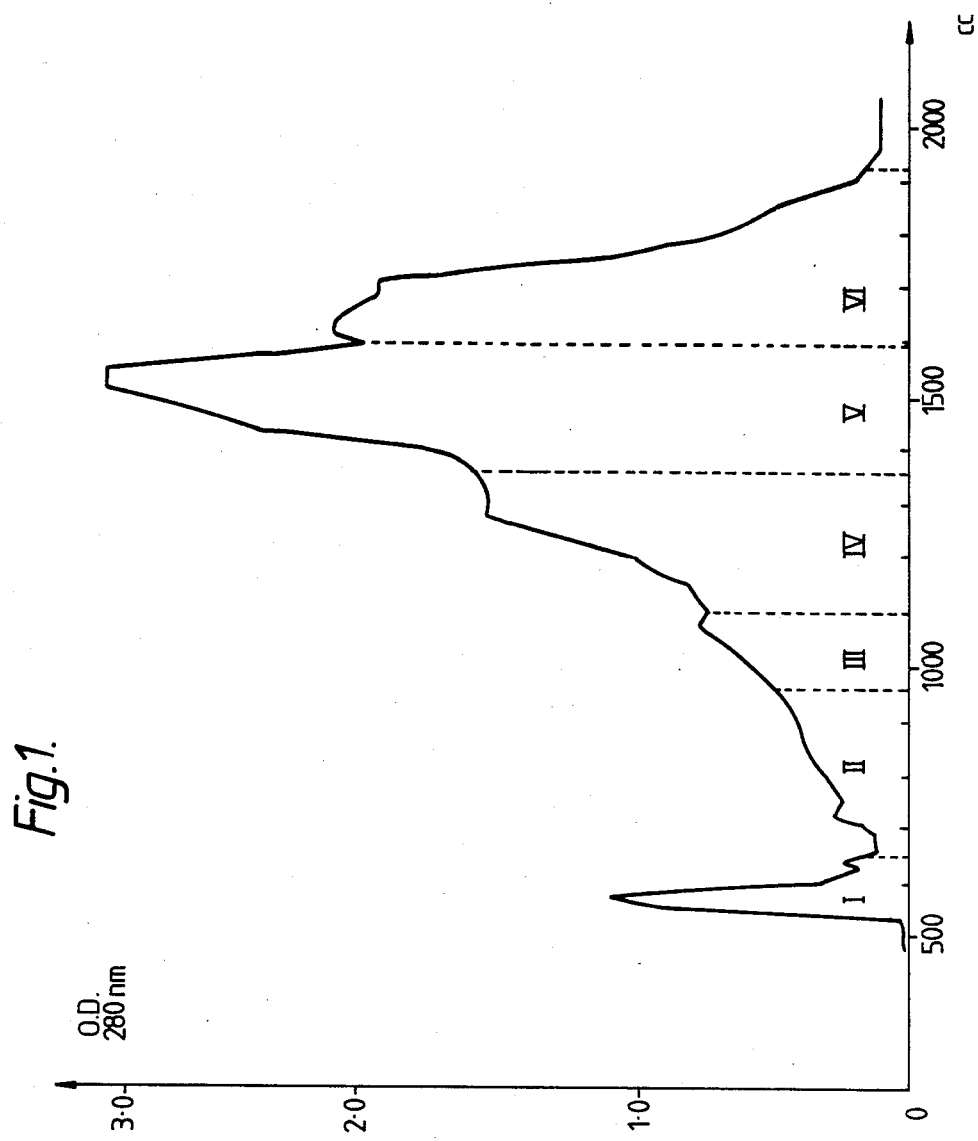

United States Patent [19]

Jolles et al.

[11] Patent Number: 4,647,554

[45] Date of Patent: Mar. 3, 1987

[54] BIOLOGICALLY ACTIVE SUBSTANCES FROM FIBRINOGEN THEIR PREPARATION AND COMPOSITIONS CONTAINING THEM

[75] Inventors: Pierre Jolles, Paris Cedex; Daniele Migliore-Samour, Le Kremlin-Bicetre; Fabienne Parker, St Maur-des-Fosses, all of France

[73] Assignee: Rhone-Poulenc Sante, Courbevoie, France

[21] Appl. No.: 744,639

[22] Filed: Jun. 14, 1985

[30] Foreign Application Priority Data

Jun. 19, 1984 [FR] France ................. 84 09560

[51] Int. Cl.[4] .............. C07K 15/06; C07K 3/10; A61K 39/39; A61K 45/05
[52] U.S. Cl. ................... 514/21; 424/88; 424/101; 435/68; 435/69; 530/382; 530/407
[58] Field of Search .............. 260/112 B, 112 R; 424/101, 88; 435/68, 69; 530/382, 407; 514/21

[56] References Cited

U.S. PATENT DOCUMENTS

| | | | |
|---|---|---|---|
| 3,912,805 | 10/1975 | Cayzer et al. | 260/112 R X |
| 4,027,013 | 5/1977 | Bick et al. | 260/112 B X |
| 4,147,765 | 4/1979 | Stephan et al. | 424/101 X |
| 4,442,655 | 4/1984 | Stroetmann | 424/101 X |
| 4,462,990 | 7/1984 | Jolles et al. | 435/69 X |

FOREIGN PATENT DOCUMENTS 49666A 4/1982 European Pat. Off. .
2382237 6/1984 France .

OTHER PUBLICATIONS

Biochim. Biophys. Acta (1969), 175(2), 282–289, Budzynski et al.
Chemical Abstracts 70 93189b.
Chemical Abstracts 98 158997p.

*Primary Examiner*—Howard E. Schain
*Attorney, Agent, or Firm*—Stevens, Davis, Miller & Mosher

[57] ABSTRACT

New immunostimulant substances are obtained by hydrolyzing reduced and alkylated bovine fibrinogen with a proteolytic enzyme and fractionating the product.

7 Claims, 5 Drawing Figures

BIOLOGICALLY ACTIVE SUBSTANCES FROM FIBRINOGEN THEIR PREPARATION AND COMPOSITIONS CONTAINING THEM

The present invention relates to biologically active substances obtained by fractionation of enzymatic hydrolysates of bovine fibrinogen, their preparation and compositions containing them.

The present invention provides novel immunostimulant substances obtained from bovine fibrinogen by reduction of the disulphide linkages followed by alkylation of the mercapto groups thus liberated, partial enzymatic hydrolysis of the product obtained, fractionation of the water-soluble hydrolysis products according to their molecular weights, and separation of a fraction of fractions having immunostimulant properties.

These new substance are immunological agents which, in particular, promote antibody production. The substances which have an average molecular weight between 500 and 7,500 have especially useful properties.

In the production of the new immunostimulant substances, the bovine fibrinogen is first reduced to break the disulphide linkages, preferably using mercaptoethanol, and the mercapto groups in the product are protected against oxidation by alkylation, preferably using iodoacetamide.

The enzymatic hydrolysis is preferably effected with trypsin, chymotrypsin or another similar enzyme, or a mixture thereof.

The water-soluble hydrolysis products are then fractionated according to their molecular weights, using any method which does not denature the hydrolysate. For example, fractionation according to molecular weight of the water-soluble fraction originating from bovine fibrinogen treated with mercaptoethanol and iodoacetamide and digested with non-pretreated trypsin yields three fractions hereinafter called IV (MJH 104), V (MJH 105) and VI (MJH 106), which have interesting biological activity.

After purification on an ion exchange column, fraction "V" (MJH 105) yields 3 active fractions [hereinafter referred to as peak 5 (MJH 176, 197, 200); peak 10 (MJH 179); and peak 11 (MJH 180)].

High performance liquid chromatography of the "peak 5" fraction then gives two zones containing active products, hereinafter denoted 4 (MJH 228) and 5 (MJH 229). One of these (zone 5) yields the substance referred to below as "MJH 335" and "MJH 336", the immunological properties of which are improved relative to those of fraction "V" itself.

The accompanying drawings illustrate the fractionation of the immunostimulant substances of the present invention, using the techniques described in the Example below, as graphs showing the variation in optical density of the eluant with the volume (or number of fractions) of eluant or retention time.

The new substances of the present invention are immunostimulant agents which promote antibody production and accelerate the phenomenon of phagocytosis.

In vitro, they have proved espically active at concentrations between 0.1 and 10 µg/ml in the test of antisheep red cell (haemolytic) antibody secretion by mouse spleen cells immunised in vivo and in the test of phagocytosis of opsonised sheep red cells by mouse peritoneal macrophages.

The Examples which follow show how the invention can be put into practice.

EXAMPLE

Reduction of bovine fibrinogen and alkylation

Fibrinogen (500 mg) is dissolved in 0.1 M tris(hydroxymethyl)aminomethane buffer (25 cc) adjusted to pH 8 with 1 M HCL, in the presence of 8 M urea. The final concentration of the protein is 20 mg/cc. Mercaptoethanol (0.2 cc) is added to the protein solution using a mole ratio of the reducing agent to the protein of 2,000 to 1. The reduction is performed at 37° C. for 3 hours under an atmosphere of nitrogen. The cysteine residues liberated are stabilised by alkylation with iodoacetamide (41 mg), while the pH of the medium is kept at 8 by adding 1 M NaOH (a few drops).

Addition of an acetone/hydrochloric acid (39:1 by volume) mixture (10 volumes) precipitates the protein after 12 hours at 4° C. Centrifugation at 15,000 rpm for 30 min. enables the precipitate to be separated. It is washed three times with the mixture described above and three times with ether. The precipitate is resuspended in water, dialysed and concentrated on a Diaflo UM 10 (Amicon) membrane, and the dialysed product is lyophilised.

The reduced and alkylated fibrinogen is dissolved in 0.1 M sodium hydroxide solution, in such a way that the final fibrinogen concentration is in the region of 1 mg/cc. The solution obtained is subjected to dialysis against 0.033 M phosphate buffer (2 liters) at pH 8 for 2 days, renewing the buffer solution 5 times.

There is thus obtained a solution at pH 8 containing soluble fibrinogen. This solution is subjected to the action of non-pretreated trypsin in such a way that the enzyme/substrate ratio is in the region of 1:00. The enzymatic hydrolysis is continued for 24 hours at 37° C., half the amount of enzyme being introduced at the start of the reaction and the remainder 4 hours after the beginning of hydrolysis.

The reaction mixture is centrifuged at 13,000 rpm for 1 hour; the supernatant is brought to dryness and then taken up in 30% strength acetic acid solution (30 cc). The mixture is subjected to centrifugation at 13,000 rpm for 30 minutes.

The clear supernatant liquid is filtered on a column of Sephadex G-50 (height 123 cm, diameter 4.5 cm), eluting with 30% strength acetic acid and collecting 2.7 cc fractions.

Working in this manner and following the chromatography by UV absorption at 280 nm, there are obtained zones which enable fractions to be defined for which the avergae molecular weight is determined. The filteration diagram is shown FIG. 1 of the accompanying drawings.

The biologically active fractions are as follows:

substane IV : fractions 1105 to 1369 cc; average molecular weight 7,000 substance V : fractions 1371 to 1593 cc; average molecular weight 2,500 substance VI : fractions 1594 to 1922 cc; average molecular weight 800.

The substance V is filtered on a column of CM Trisacryl (IBF registered trademark) (height 110 cm, diameter 2.2 cm), eluting with a 0.01 M Tris-HCl [tris(hydroxymethyl) aminomethane, HCl] buffer solution at pH 3.5 and collecting 3.1-cc fractions.

Figure 2:
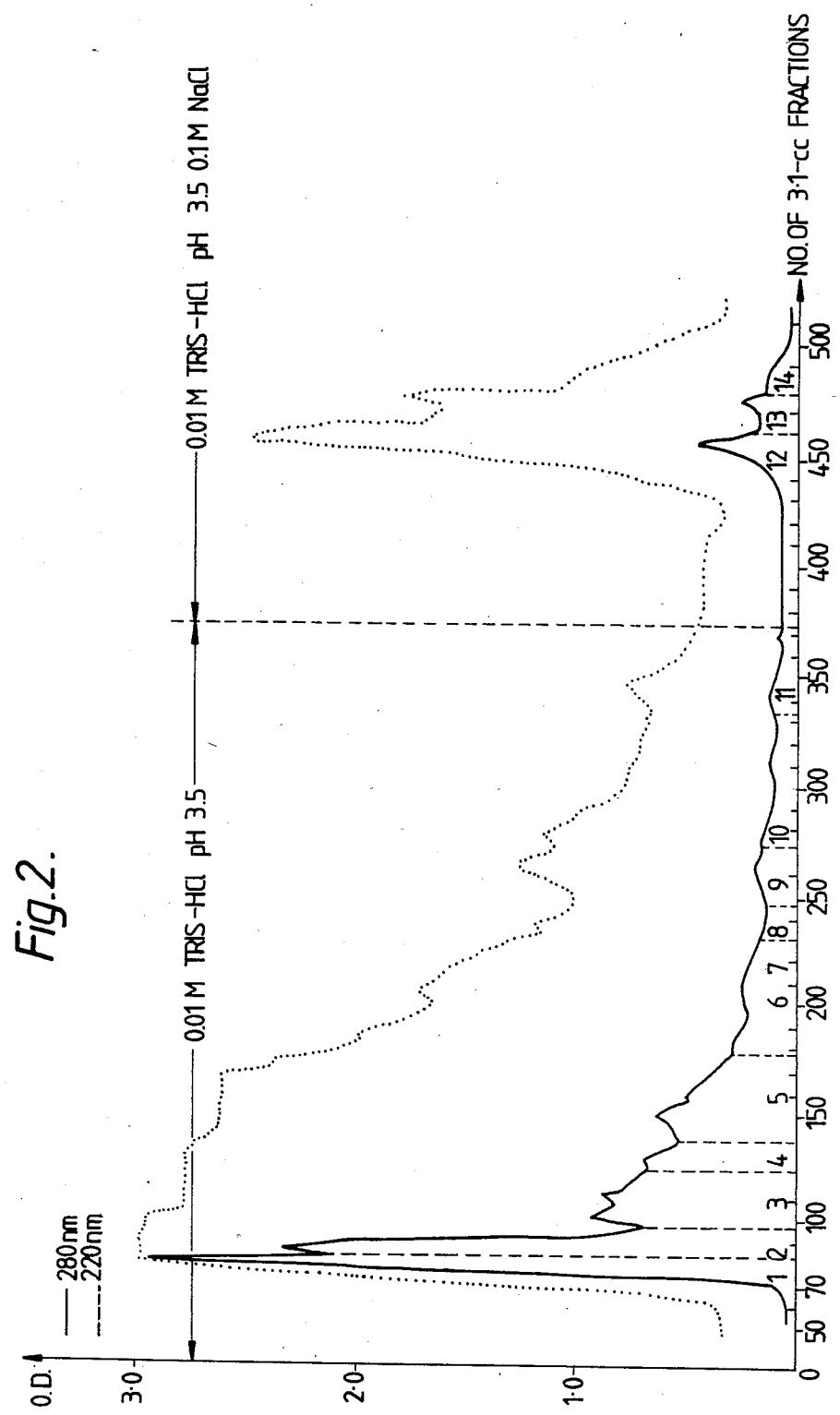

The filtration diagram is shown in FIG. 2, in which the fraction numbers appear as abscissae and the optical densities at 280 and 220 nm as ordinates.

14 fractions are collected, among which the fractions from 430 to 558 cc, 850 to 1042 cc and 1043 to 1153 cc yield, respectively, the active substances referred to as "peak 5" (MJH 176, 197 and 250), "peak 10" (MJH 179) and "peak 11" (MJH 180).

The "peak 5" fraction is purified by reversed phase HPLC on a semi-preparative column (WATERS C18-μ-bondapak column, the length of which is 30 cm and the diameter 7.8 mm. 0.5-cc fractions are collected, the elution rate being 1 cc/minute. At the start, the column is buffered with 0.1% strength trifluoroacetic acid (TFA) (eluant A).

An eluant containing TFA (0.1% by volume) and acetonitrile (70%) (eluant B) is prepared.

The "peak 5" fraction is dissolved in 01.% strength TFA (500 μl).

The elution is performed using a linear elution gradient, proceeding according to the following table:

| Time (minutes) | Eluant A | Eluant B |
|---|---|---|
| 0 | 100 | 0 |
| 60 | 0 | 100 |

Figure 3:
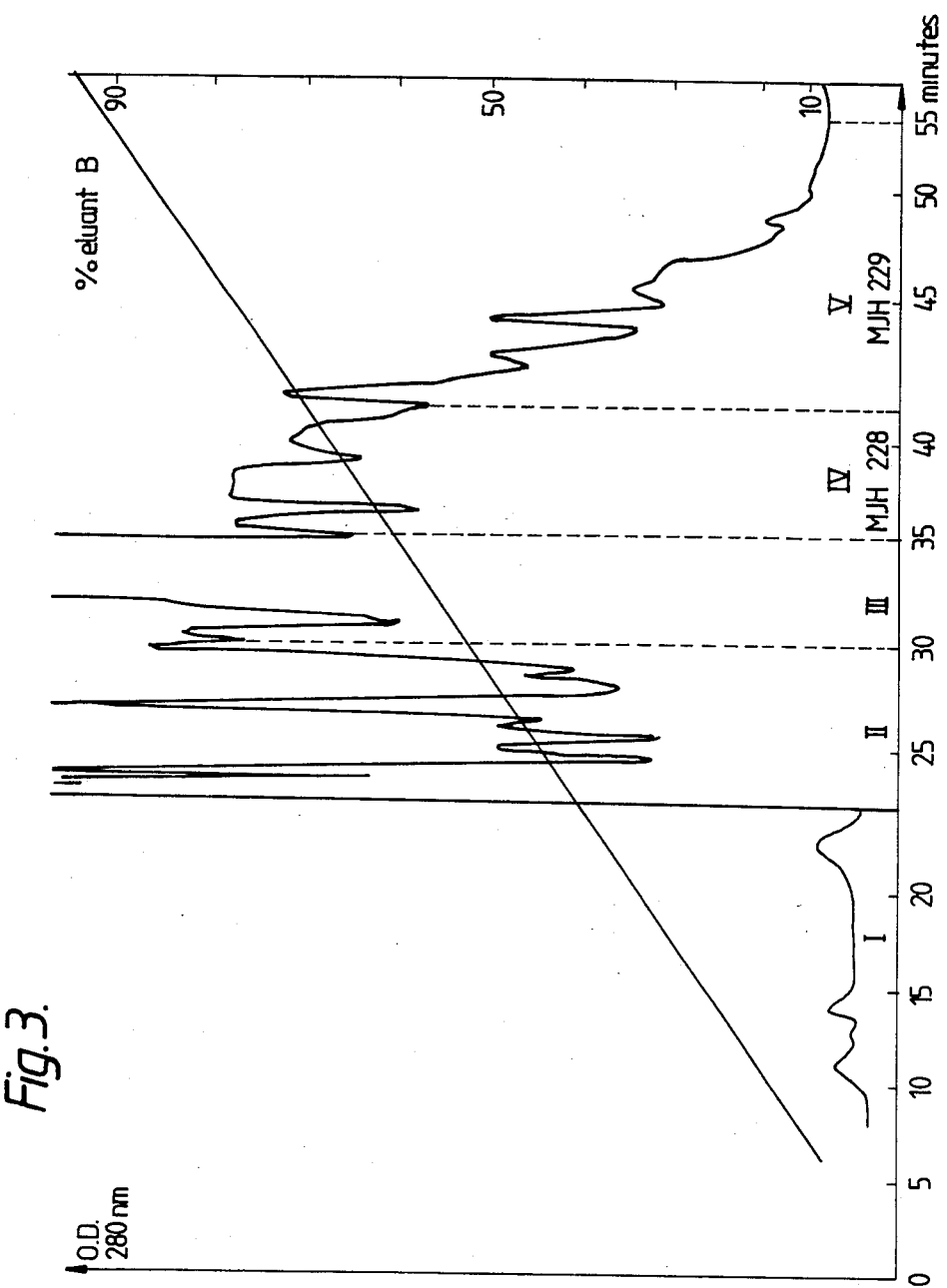

The elution diagram is shown in FIG. 3. The elution is followed by measuring the absorption at 280 nm and 220 nm.

The elution diagram includes 5 zones, the most important fractions of which are zone IV (MJH 228) and zone V (MJH 229) arising from the elution mixture with a retention time of, respectively, between 36 and 41 minutes and 41 and 55 minutes.

Fraction MJH 228 is again purified by HPLC on a column of the same type as that used previuosly, collecting 0.5-cc fractions, the elution rate being 1 cc/minute.

The same eluants are used as above.

The elution is performed using a hyperbolic elution gradient no. 7 (WATERS), proceeding according to the following Table:

| Time (minutes) | Eluant A | Eluant B |
|---|---|---|
| 0 | 100 | 0 |
| 10 | 90 | 10 |
| 70 | 0 | 100 |

Figure 4:
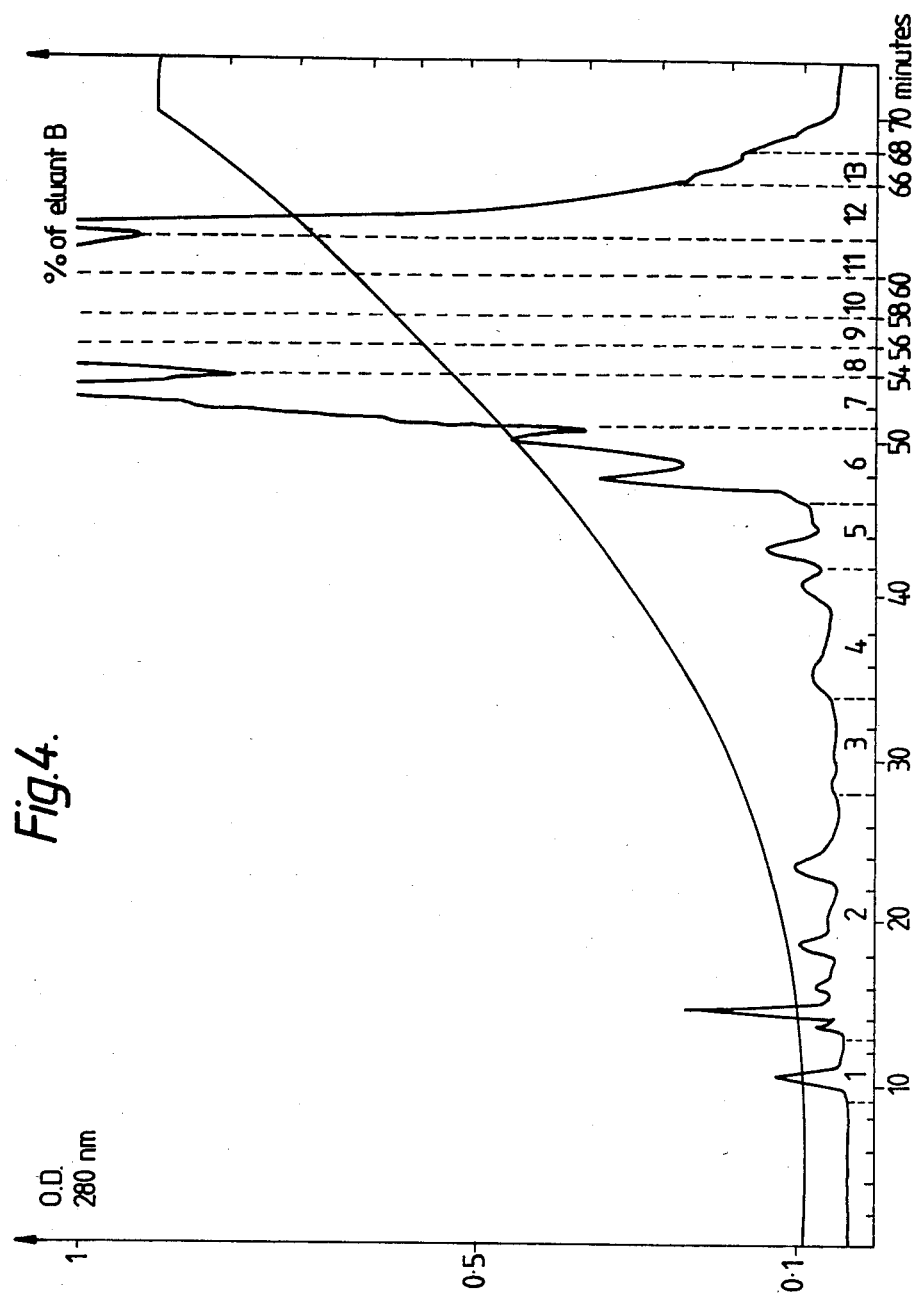

The elution diagram is shown in FIG. 4.

The elution diagram includes 13 peaks.

The fractions eluted between 51 and 54 (peak 7) 54 and 56 (peak 8), 61 and 63 (peak 11) and 63 and 66 minutes (peak 12) contain, respectively, the active substances MJH 257, MJH 258, MJH 261 and MJH 262.

Fraction MJH 229 is again purified by HPLC on a column of the same type as that used above, collecting 0.5-cc fractions, the elution rate being 1 cc/minute.

The same eluants are used as above.

Figure 5:
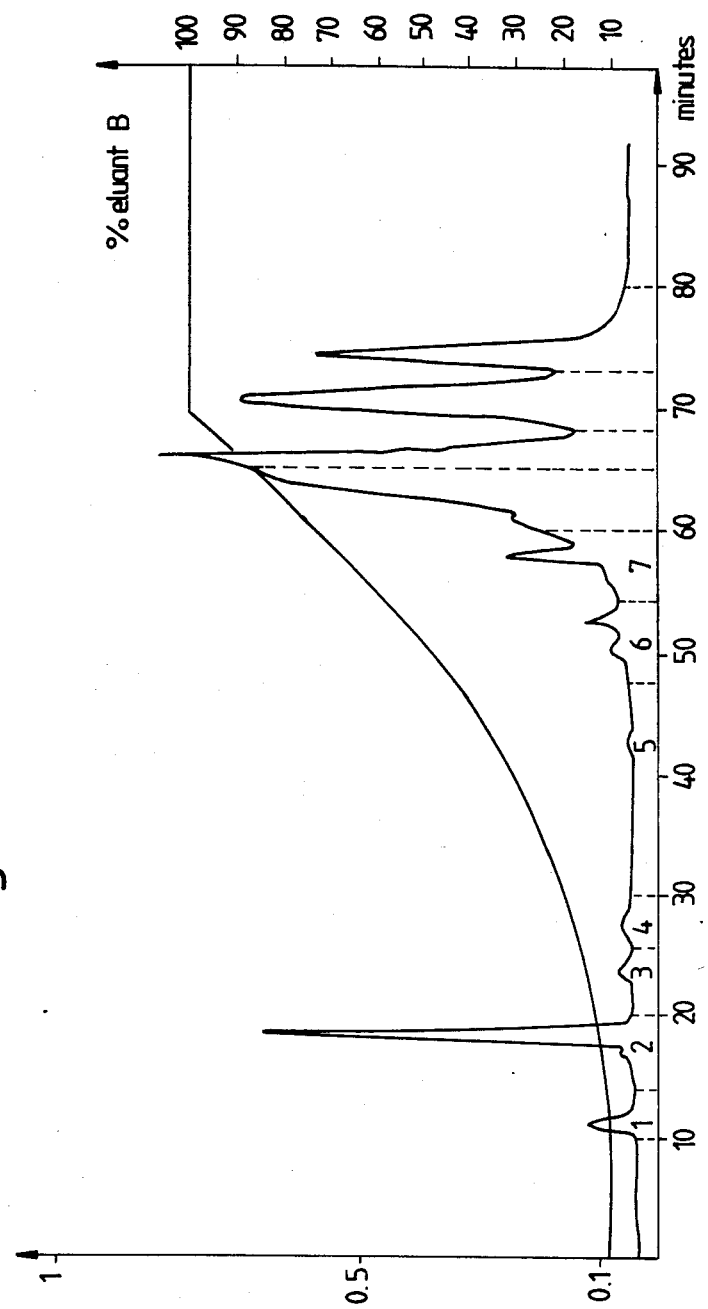

The elution is performed using a hyperbolic elution gradient (WATERS gradient 7), proceeding according to the table used for MJH 228 above. The elution diagram is shown in FIG. 5. The elution diagram contains 12 fractions. The fractions eluted between 60 and 65 minutes, 65 and 68 minutes and 68 and 74 minutes contain, respectively, the substances MJH 253, MJH 254 and MJH 255.

The fraction containing the product MJH 254 is again purified by HPLC on a column of the same type as that used above, collecting 0.5-cc fractions, the elution rate being 1 cc/minute.

The same eluants are used as above.

The elution is performed proceeding according to the following table:

| Time (minutes) | Eluant A | Eluant B | Gradient |
|---|---|---|---|
| 30 | 60 | 40 | isocratic |
| 70 | 0 | 100 | linear |

The elution diagram includes 3 main zones.

Fractions eluted between 15 and 20 minutes, 20 and 24 minutes and 46 and 60 minutes contain, respectively the substances MJH 299, MJH 301 and MJH 305.

The fraction MJU 299 is again purified by HPLC on a column of the same type as that used above, collecting 0.5-cc fractions, the elution rate being 1 cc/minute.

The same eluants are used as above.

The elution is performed proceeding according to the following table:

| Time (minutes) | Eluant A | Eluant B | Gradient |
|---|---|---|---|
| 30 | 80 | 20 | isocratic |
| 75 | 60 | 40 | linear |

The fractions eluted between 52 and 53 minutes and between 54 and 57 minutes contain, respectively, the active substances MJH 335 and 336.

The present invention also provides pharmaceutical compositions which can be used in therapy containing a substance according to the present invention in combination with one or more diluents or adjuvants which are compatible and pharmaceutically acceptable.

These compositions can be used as vaccine adjuvants (for example for anti-influenza vaccine composed of haemagglutinating sub-units, anti-poliomyelitis vaccine with inactivated virus, antimalarial vaccine), injected simultaneously with the antigen (viral, bacterial, parasitic, fungal, tumour) in respect of which it is desired to increase antibody production or specific cell reactivity.

These pharmaceutical compositions can also be used as non-specific immunostimulants, with a view to increasing the resistance of the host (man or domestic animal) to infections or in anti-tumour immunotherapy.

As adjuvants, the new substance can be administered either in aqueous solution, or in oily emulsion, or alternatively in the form of liposomes with the antigen in respect of which it is desired to obtain an increased or improved immune response, by the route used for this antigen and in proportions which vary between 0.01 and 10 times the amount of antigen with which they are mixed before being injected.

For application as non-specific immunostimulants, the new substances can be administered intravenously, intramuscularly, subcutaneously, intranasally, and optionally orally or rectally, either in aqueous solution or in oily emulsion, or alternatively in the form of liposomes. In this case, the dose of substance according to the invention which is administered is generally between 0.01 and 10 mg/kg. In human therapy, the daily dosage depends on the effect sought. It can be between 0.5 and 10 mg for an adult.

Solid compositions for oral administration can be tablets, pills, powders, or granules.

Liquid compositions for oral administration can be pharmaceutically acceptable emulsions, solutions, suspensions, syrups, or elixirs.

The compositions for parenteral or intranasal administration can be sterile aqueous solutions, or suspensions or emulsions.

Sterilisation can be carried out in several ways, eg. by means of a bacteriological filter or by incorporating sterilising agents. The solid compositions made sterile by irradiation ($\beta$-rays) can be dissolved in sterile water or any other injectable sterile medium, optionally at the time of use.

The compositions for rectal administration are suppositories.

The example which follows illustrates a composition according to the invention.

EXAMPLE

By the customary technique, a liquid composition which can be administered intravenously is prepared having the following composition:
substance MJH 257: 10 mg;
injectable solution: 5 cc.

We claim:

1. An immunostimulant substance obtained from bovine fibrinogen by reduction of the disulphide linkages followed by alkylation of the mercapto groups thus liberated, enzymatic hydrolysis of the product obtained with trypsin, chymotrypsin or both trypsin and chymotrypsin, fractionation of the water-soluble hydrolysis products having an average molecular weighr in the range 500 to 7500 by gel filtration, and separation of a fraction or fractions having immunostimulant properties.

2. An immunostimulant substance according to claim 1 wherein the enzymatic hydrolysis is effected for about 24 hours at about 37° C. using an enzyme substrate ratio of about 1:100.

3. An immunostimulant substance according to claim 1 having an average molecular weight of about 2500.

4. An immunostimulant substance according to claim 1 wherein the fractionation of the hydrolysis products is effected by filtration on Sephadex G-50, eluting with 30% aqueous acid.

5. An immunostimulant substance according to claim 1 wherein the fractionation is followed by high performance liquid chromatography.

6. An immunostimulant substance according to claim 1 wherein the reduction of the disulphide linkages of the fibrinogen is effected with mercaptoethanol and the alkylation of the mercapto groups is effected with iodoacetamide.

7. A pharmaceutical composition comprising an effective amount of an immunostimulant substance according to claim 1 is association with a compatible, pharmaceutically acceptable diluent or adjuvant.

* * * * *